(12) United States Patent  
Griffin (10) Patent No.: US 7,665,600 B1
(45) Date of Patent: Feb. 23, 2010

(54) DENTAL FLOSS ENVELOPE PACKAGE WITH CUTTER ELEMENT

(75) Inventor: Bradley P. Griffin, Greenville, NC (US)

(73) Assignee: Practicon, Inc., Greenville, NC (US)

( * ) Notice: Subject to any disclaimer, the term of this patent is extended or adjusted under 35 U.S.C. 154(b) by 220 days.

(21) Appl. No.: 11/824,897

(22) Filed: Jul. 3, 2007

Related U.S. Application Data

(60) Provisional application No. 60/858,596, filed on Nov. 13, 2006.

(51) Int. Cl.
*A61B 19/02* (2006.01)
*A61C 15/00* (2006.01)

(52) U.S. Cl. .................. 206/63.5; 132/324; 206/388

(58) Field of Classification Search ............. 206/63.5, 206/388; 132/321, 323–329
See application file for complete search history.

(56) References Cited

U.S. PATENT DOCUMENTS

| | | | |
|---|---|---|---|
| 3,094,209 A | 6/1963 | Krupp | |
| 4,327,755 A | 5/1982 | Endelson | |
| 4,579,221 A | 4/1986 | Corella | |
| 4,852,728 A | 8/1989 | Court | |
| 4,881,560 A | 11/1989 | Blank et al. | |
| D309,959 S | 8/1990 | Endelson et al. | |
| 4,972,946 A * | 11/1990 | Whittaker | 132/324 |
| 5,190,200 A | 3/1993 | Hammerlund | |
| 5,566,692 A | 10/1996 | Thornton | |
| 5,582,194 A | 12/1996 | Dolan | |
| 5,649,659 A * | 7/1997 | Saunders | 132/325 |
| 5,678,580 A | 10/1997 | Sherman | |
| 5,772,439 A | 6/1998 | Yamaoka et al. | |
| 5,787,907 A | 8/1998 | Endelson | |

* cited by examiner

*Primary Examiner*—Bryon P Gehman
(74) *Attorney, Agent, or Firm*—K&L Gates LLP (57) ABSTRACT

A dental floss package for containing and dispensing a length of floss therefrom, the package including a dispensing envelope formed of thin paper-type material that includes two flat side walls folded over one another in overlapping relation to lie closely adjacent one another, a flap portion joined to one of the side walls and folded over the other side wall, and a cutter element is mounted on the dispensing package. A multi-use supply of dental floss is contained within the dispensing envelope, and has one exposed end thereof passing out through an exit opening in the dispensing envelope. An outer sleeve may be provided over the dispensing envelope, and the floss may be contained in a plastic pouch.

13 Claims, 6 Drawing Sheets

DENTAL FLOSS ENVELOPE PACKAGE WITH CUTTER ELEMENT

CROSS-REFERENCE TO RELATED APPLICATION

This application is entitled to the benefit of, and claims priority to, provisional U.S. Patent Application Ser. No. 60/858,596 filed Nov. 13, 2006, and entitled "DENTAL FLOSS PACKAGE," the entirety of which is incorporated herein by reference.

BACKGROUND OF THE INVENTION

It is a well known fact that a majority of people suffer from periodontal disease in varying degrees. Such disease is the result of the accumulation of plaque between the teeth and along the gum line, initially leading to inflamed gums or gingivitis, and later periodontitis, a condition marked by gum recession and ultimately, tooth loss.

To avoid, or at least alleviate, the accumulation of plaque, most dentist recommend that dental floss be used after each meal to offset the accumulation of plaque. While there are a large number of commercial packages for containing and dispensing dental floss, the great majority of these packages are intended to be maintained in a compartment in the bathroom, such as a medicine cabinet or a drawer. As a result, they are not intended to be portable and they are seldom carried by a person for use outside the home.

In Dolan U.S. Pat. No. 5,582,194, a portable floss package intended for a single use application is disclosed. The package consist of three overlapping panels, and a small length of dental floss which is maintained within the package by an adhesive to which both ends of the length of dental floss are attached. Thus, the length of dental floss is maintained completely within the confines of the package until it is used, at which time the single length of dental floss is pulled away from the adhesive and used, and the package is disposed of. Obviously, this type of packaging results in a substantial per use expense since each package is capable of only one use, and it is also impractical to the extent that a person using this type of dental floss packaging must carry a large number of single-use packages. A somewhat similar single used package of dental floss is also disclosed in Court U.S. Pat. No. 4,852,728, and in Corella U.S. Pat. No. 4,579,221. In U.S. Pat. No. 5,190,200 to Hammerlund, a recyclable dental floss dispenser is disclosed which includes a large three-dimensional box in which the dental floss is contained. The box is formed with front and back walls, two wide side walls and top and bottom walls, and a large closure flap and a hang tab that permits the package to be hung from a hook or the like. As a result, the package in Hammerlund is large and bulky, it is not pliable because of its box like shape, and it does not lend itself to being portable and easily carried in an a wallet or small handbag.

It is also been proposed to package a larger supply of dental floss in a casing which is similar in size and shape to a credit card. In Sherman U.S. Pat. No. 5,678,580, the supply of dental floss is wrapped around a core member which appears to be rigid, and the core member is slideably housed within a protective case and some form of a stop is provided in the casing to limit outward movement of the core and the floss wrapped around the core. Another type of credit card floss dispenser is disclosed in Endelson U.S. Pat. No. 4,327,755. In this dispenser, a plastic material is used to form a base panel having a peripheral ridge extending there around to define a rectangular well, and a top panel is attached to the peripheral ridge of the base panel to form a fully contained compartment within the interior of the package. A supply of dental floss is disposed within the enclosed compartment, and an end of the dental floss extends outwardly from the enclosed compartment through an opening so that a desired length of the dental floss can be pulled from the package and then cut using a cutter formed on one edge of the package. Other similar packages are disclosed in Endelson U.S. Pat. Nos. 4,881,560, 5,772,439, and 5,787,907.

While these credit card-type dispensers are relatively small and functional, they have the disadvantages of being very rigid and therefore less susceptible to good portability where some flexibility or resiliency is required, and, in general, it appears that they are relatively expensive to manufacture.

SUMMARY OF THE INVENTION

Briefly summarized, the present invention provides a dental floss package for containing and dispensing a length of floss therefrom, the package including a dispensing envelope formed of relatively thin paper-type material that includes two flat side walls folded over one another in overlapping relation to lie closely adjacent one another. The two overlapping side portions are joined directly to one another along side edges thereof. A flap portion is joined to one of the side walls and folded over the other side wall to extend in parallel relation along the outer surface of the other side wall, and the flap is secured to such outer surface. A cutter element is mounted on the dispensing package at an exposed location, and an exit opening is formed in the dispensing envelope through which dental floss can pass. The package also includes a supply of dental floss contained within the dispensing envelope, and one exposed end of the dental floss passes out through an exit opening in the dispensing envelope and over an outer portion of the dispensing envelope to the cutter element, whereby a desired length of the dental floss may be withdrawn from the dispensing envelope by grasping such exposed end of the dental floss, pulling the desired length of dental floss from the package and cutting it using the cutter element.

In the preferred embodiment of the present invention, the side walls of the dispensing envelope are generally rectangular in shape with three side edges thereof glued together and with the other side edge being open, and wherein the flap portion is integrally formed with one of the side walls and is folded over the open side edge of the side walls. The cutter may be secured to the other side wall at a location under the flap portion, and an aperture may be formed in the flap portion where the cutter is located so that the cutter is exposed through the opening in the flap.

The exit opening formed in the dispensing package is preferably located at one side edge of the side walls of the dispensing package at the point where the flap portion is folded over the other side wall, and the dental floss is formed in a flat spiral. The dental floss may be contained within a plastic pouch having an opening therein through which the dental floss can pass to the exit opening in the dispensing envelope.

An adhesive strip is preferably located along the other side wall adjacent the open end of the dispensing package, and the cutter element is secured to the other side wall by a portion of the adhesive strip. The flap portion of the dispensing envelope may be secured to the other side wall by another portion of this adhesive strip.

The dispensing envelope may be slideably contained in an outer sleeve whereby the dispensing envelope can be maintained in the outer sleeve when not in use and easily removed from the outer sleeve when it is to be used.

In an alternate embodiment of the present invention, the flap portion is formed with a second opening, and an adhesive is applied to the other side wall beneath the second opening so that the adhesive will be exposed through the second opening, whereby the end of the dental floss can be held in place by engagement with such exposed adhesive.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

DESCRIPTION OF THE PREFERRED EMBODIMENTS

Looking in more detail at the accompanying photographs, one embodiment of the present invention is shown in FIGS. 1-5, and it includes a dental floss package 10 that is composed of four basic elements, namely a flat coil of conventional dental floss 12, a pouch 14 in which the floss 12 is carried, an inner dispensing envelope 16, and an outer sleeve 32, all of which will now be described in more detail and with reference to the accompanying photos.

Figure 3:
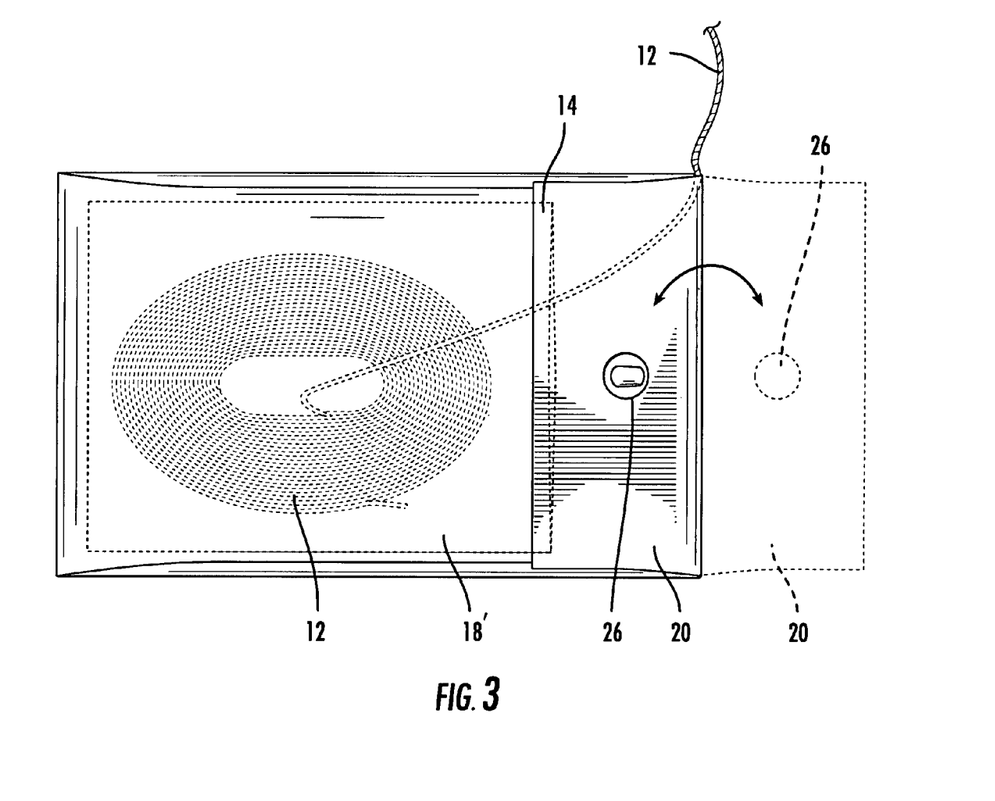
FIG. 3 is a top plan view of the inner dispensing envelope.
Figure 4:
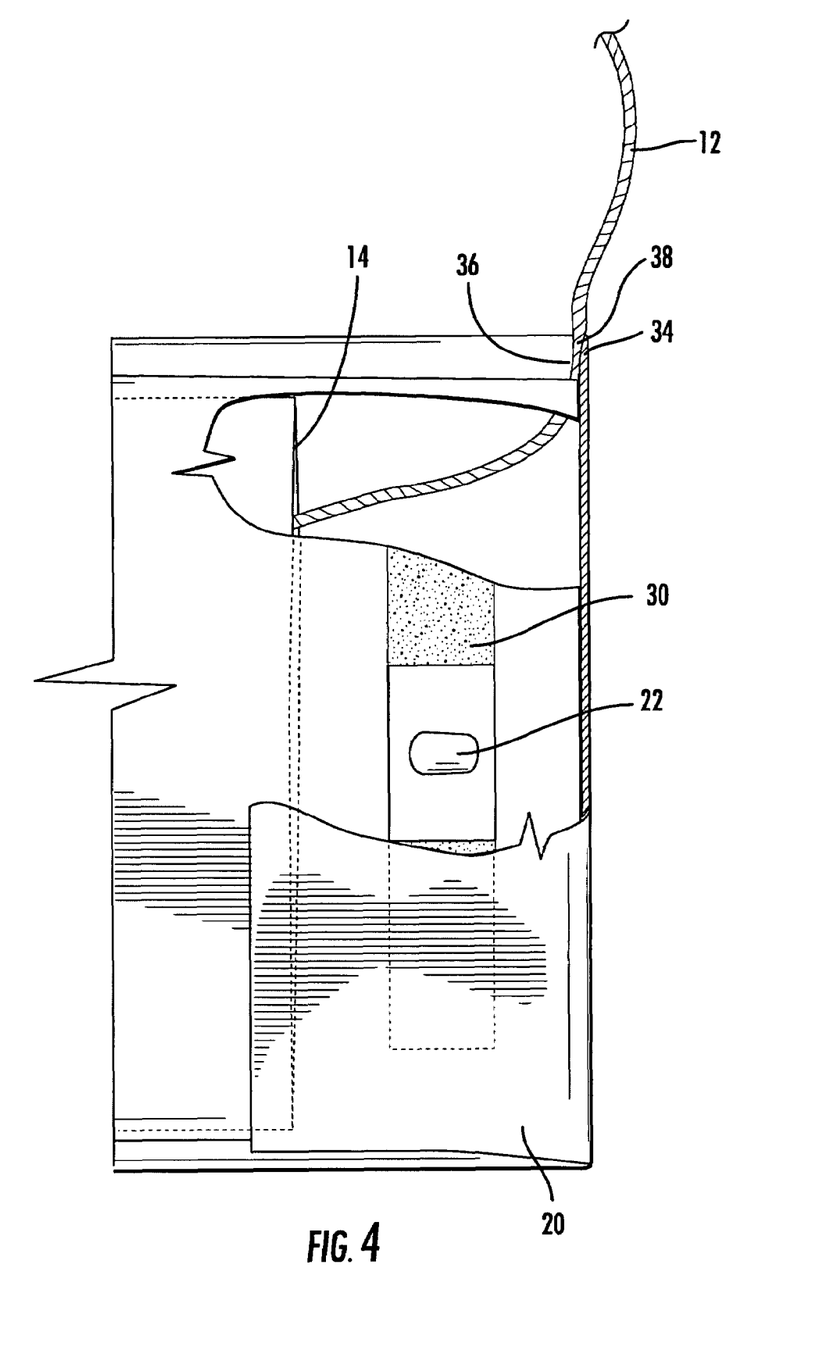
FIG. 4 is a top plan view of the top portion of the inner dispensing envelope, but partially cut away to illustrate the inside of the inner dispensing envelope.

The flat coil of dental floss 12, which is best seen in FIGS. 3 and 4, can be made by coiling any conventional dental floss of a single or multiple filament construction upon itself in a manner that makes an approximate circular or spiral "coin" shape with the filament wrapping layer by layer from inside to outside. The thickness of the floss 12 may be of any desired dimension, but it will often be controlled in its manufacturing process by a fixed spooling thickness having an approximate width of 1/16" or approximately two strands of standard filament in order to fit within the flat confines of the pouch 14 and the dispensing envelope 16 during subsequent assembly. A suitable dental floss wax (not shown) may be applied to the floss 12 prior to coiling to assist in the adherence of the floss layers into a non-tangling, flexible flat floss 12 that remains intact as a flat spiral coil after manufacturing, and during subsequent handling, assembly and consumption. The amount of wax may be adjusted to suit assembly requirements and market preferences, and, if desired, a flavor (not shown) may also be applied to the floss prior to coiling to suit market preferences. Further, as part of the coiling process, and as best seen in FIG. 3, an approximate 3-inch length of the floss 12 at the center of the coil, which may be described as the starting end, is left to freely extend from the center of the coil towards and past the outside diameter of the coil for eventual grasping and withdrawal from the pouch 14, as will be described in greater detail below. Accordingly, after subsequent assembly in the pouch 14 and envelope 16, pulling the end of the floss 12 that is closest to the center of the floss 12 will cause the floss 12 to be unwound from inside to outside until the floss supply is exhausted. Depending on the amount of the multi-use supply floss 12 contained in the coil, and the dimensions of the floss 12, the floss 12 can be by varied by forming it into shapes other than circular, such as, for example, it may be deformed into a flat elliptical shape (not shown) upon insertion into a pouch 14 having a more narrow width. The entirely flat spiral in which the floss 12 is formed has a thinness corresponding to the very thin diameter of the floss filament (e.g. 1/16-inch), which lends itself to fitting into the small height of the inner dispensing envelope 16 to thereby contribute to the desired overall thinness of the entire package 10.

The pouch 14 is preferably made of plastic, but it can be made from any other suitable material. It preferably has a rectangular shape as best seen in FIGS. 3 and 4, and it is sealed on three of its four sides, with the fourth side (the upper side in FIGS. 3 and 4) left open for inserting the floss 12 into the pouch 14 during the manufacturing process, and for permitting the floss 12 to be withdrawn from the pouch 14 as will be described in greater detail below. It will be understood that in some applications it may be possible to load the floss 12 directly into the envelope 16, without the pouch 14. However, in manufacturing and assembling the dental floss package 10, the pouch 14 offers some advantages. It will also be understood that other shapes of the pouch 14 may also be used so long as it can contain the floss 12 and permit an end of the floss 12 to pass out of the pouch 14. When the floss 12 is inserted into the pouch 14, the aforesaid starting end of the floss 12 that extends from the center of the coil can extend freely outside the open side of the pouch 14 for eventual grasping and withdrawal from the pouch 14. Alternatively, the starting end of the floss 12 that extends from the center of the coil may be pulled through an opening (now shown) formed in the walls of the pouch 14. The pouch 14 may be of any suitable dimension that will properly fit within the confines of the dispensing envelope 16.

Figure 5:
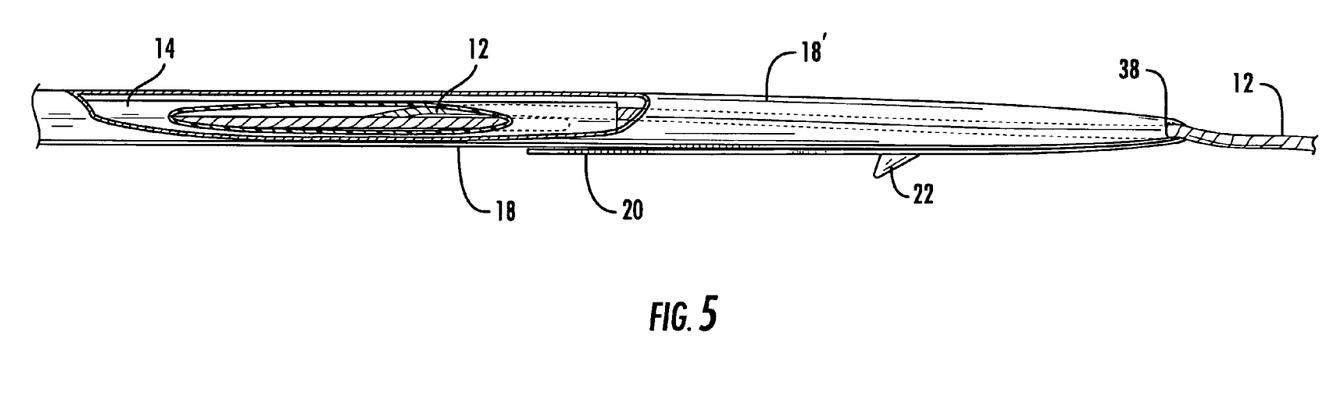
FIG. 5 is a side view of the inner dispensing envelope, partially cut away to show the inside of the inner dispensing envelope; and with the height of the inner dispensing envelope somewhat exaggerated for clarity of illustration.

The dispensing envelope 16 and the outer sleeve 32, which is best seen in FIGS. 1-5, are preferably made from a paper-like material, such as a water-resistant and tear resistant synthetic paper. In the preferred embodiment of the present invention, it has been found that a paper-like polypropylene substrate sold under the trademark SYNCARTA provides the desired stiffness to maintain the integrity of the envelope 16 and the outer sleeve 32 while still being pliable in use, but the dispensing envelope and the outer sleeve may be made from any other similar substrates and that has these characteristics. Paper, which is less expensive, may also be used, but it is not as desirable as the aforesaid polypropylene substrate. Preferably, the envelope 16 is rectangular in shape, and it has two flat side walls 18 and 18' that may be made from one piece of material and folded over one another in overlapping relation to lie closely adjacent one another as best seen in FIG. 5. The overlapping side walls 18 and 18' are joined together, preferably by gluing, along three edges, with the upper edges of the side walls 18 and 18' as shown in FIGS. 3 and 4 being unsealed and open. The dispensing envelope 16 is preferably rectangular in shape, but it will be understood that other shapes may be used so long as the floss 12 and the pouch 14 can be contained therein while permitting an end of the floss 12 to be pulled out of the dispensing envelope 16.

One side wall 18 is integrally formed with a flap 20 and it is folded along a fold line 34 extending parallel to the upper edge 36 of the other side wall 18' to extend over the outer surface of the other side wall 18' to close and seal the open end of the side walls 18 and 18'. Accordingly, the flap 20 may be disposed in its open position as shown in dotted lines in FIG. 3 to permit the pouch 14 and coil of dental floss 12 to be inserted into the dispensing envelope 16 during the manufacturing process, after which the flap 20 is folded to its closed position as shown in full lines in FIG. 3 to retain the pouch 14 and coil of dental floss 12 within the confines of the dispensing envelope 16.

As best seen in the cut-away portion of FIG. 4, the fold line 34 is located closely adjacent the upper edge 36 of the other side wall 18'. As a result, when the flap 20 is folded about the fold line 34 to its closed position, a narrow exit opening 38 between the fold line 34 and the upper edge 36 will be left at the upper left-hand corner of the dispensing envelope 16, and the end of the floss 12 within the dispensing envelope can be passed out from the interior of the dispensing envelope through the exit opening 38. The narrow exit opening 38 creates frictional resistance to the floss 12 as it is withdrawn from the package, and this resistance assists in untangling any knot or backlash from the coil of the floss 12 as the floss 12 is withdrawn from the dispensing envelope 16. Additionally, this resistance also helps prevent the floss 12 from backtracking or withdrawing back into the dispensing envelope 16.

The side wall 18' of the dispensing envelope 16 is preferably provided with an integrated adhesive strip or line of glue 24 that extends laterally along the outer surface of side wall 18' adjacent the open end of the dispensing envelope as shown in FIG. 4 so that it is located beneath the flap 20 when the flap 20 is in its closed position. The line of glue 24 is preferably used to secure a conventional cutter blade 22 to the side wall 18', and to also extend beyond the cutter blade 22 and serve as the glue for engaging and maintaining the flap 20 in its closed position after the pouch 14 and the coil of dental floss 12 have been inserted into the dispensing envelope 16. However it will be understood that the adhesive strip or glue 24 may be located on the inside of the flap 20, and the cutter blade 22 can be secured to the side wall 18' using a separate supply of glue or other type of securement. The flap 20 is formed with an access opening 26, preferably in the form of first die-cut hole, and the access opening 26 is located in the flap 20 at a location corresponding the location of the cutter blade 22 so that the cutter blade 22 is exposed through the access opening 26 when the flap 20 is in its closed position as shown in FIGS. 3 and 4, thus allowing the withdrawn end of the floss 12 to be cut by the cutter blade 22 as will be explained in greater detail below.

Figure 6:
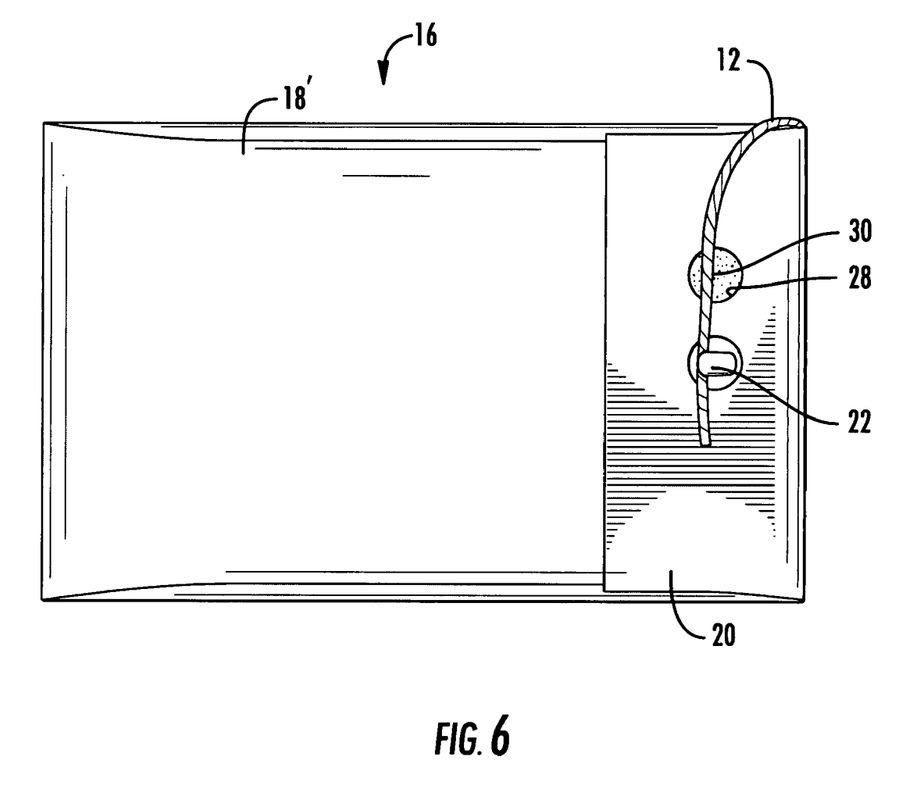
FIG. 6 illustrates an alternate embodiment of the inner dispensing envelope.

Additionally, in an alternate embodiment of the present invention, a second small die-cut hole 28 may be formed in the flap 20, and it is located within the area of the flap 12 to expose an adhesive 30 so that this exposed adhesive 28 may be used to capture and hold the loose end of the floss 12 after it has been cut by the cutter blade 22, so as to temporarily secure the loose end of the floss 12 and prevent inadvertent floss withdrawal during storage and transport, all as best shown in FIG. 6. Although it will be understood that the hole 32 and the adhesive 28 can be located anywhere along the flap 20, it is preferred that hole 32 and the adhesive 28 be positioned to lie in the path of the floss 12 as it passes from the exit opening 38 in the dispensing envelope 16 to the cutter 22 to thereby make is easier to capture and hold the loose end of the floss 12 after it has been cut.

Figure 1:
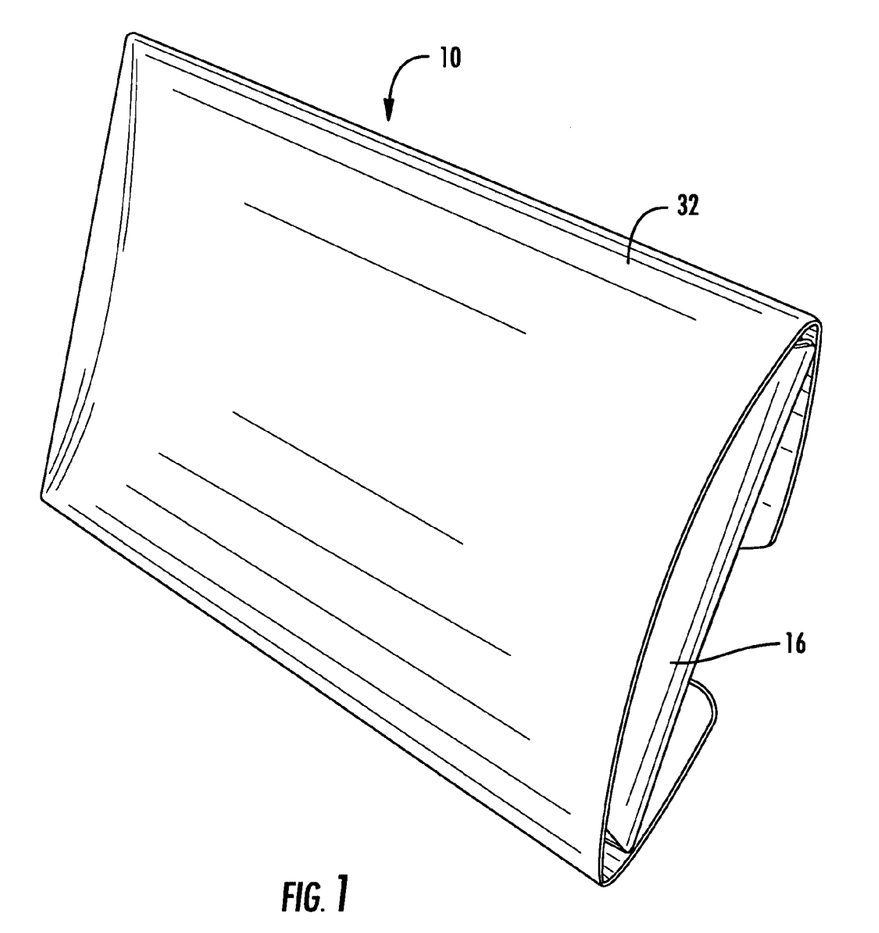
FIG. 1 is perspective view of one embodiment of the dental floss dispensing package according to the present invention.
Figure 2:
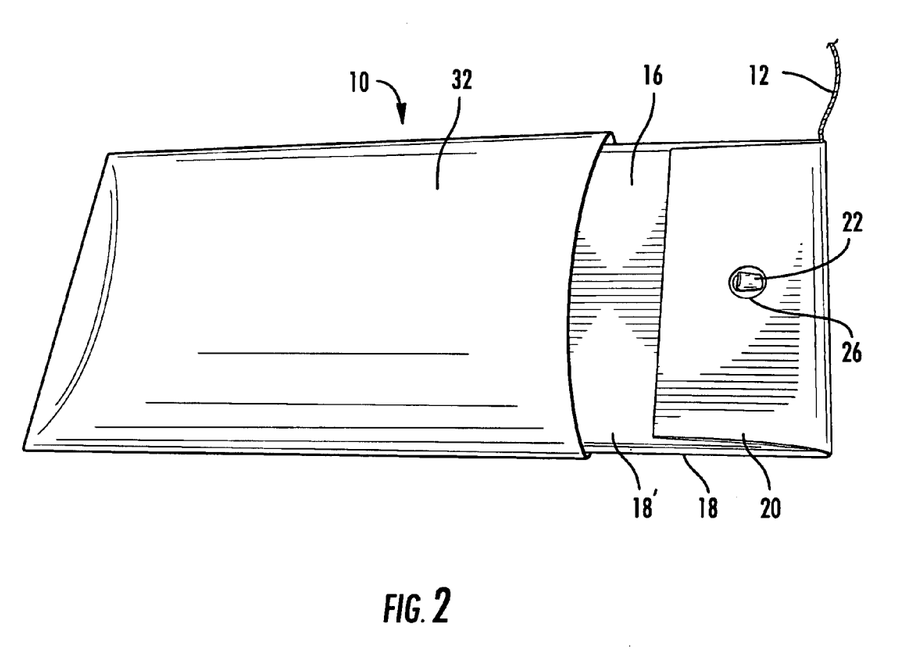
FIG. 2 is a perspective view like FIG. 1 and showing the inner dispensing envelope partially withdrawn from the outer sleeve.

In the preferred embodiment of the present invention, the floss dispensing package 10 includes an outer sleeve 32 that has a rectangular shape corresponding to the shape of the dispensing envelope 16, but that is slightly larger than the dispensing envelope 16 so that the dispensing envelope 16 can be slideably contained within the outer sleeve 32 through the open end thereof. Accordingly, when the dispensing envelope 16 is not in use it can be slid into the outer sleeve 32 and maintained in a covered and sanitary disposition, and when it is desired to dispense floss 12 from the dispensing envelope 16, it can be easily pulled out of the outer sleeve 32 as illustrated in FIG. 2.

If desired, the dental floss package 10 of the present invention may be contained within an individual cellophane wrapping (not shown) for a more sanitary presentation. Additionally, the paper-like material from which the dental floss package 10 is made lends itself nicely to inexpensive printing on the flat surfaces of the packages. By way of example, the packages 10 may be sold to dentist as promotional items for the dentist to use with his or her patients, and the outer package could be printed with an attractive design on one of the side walls 18 or 18', and the other side wall could be printed with a form for the patient to enter the time and date of the patient's next appointment. The dispensing envelope could be printed with the name and address of the dentist, and with such other information that the dentist may want. It will be understood that these are representative samples only, and a wide variety of printing options would be available to the manufacturer of the packages 10 depending on the anticipated users of the packages 10.

The above described dental floss package 10 allows users to dispense and cut a continuous length of dental floss 12, as needed, from the dispensing envelope 16 that resembles a small, sealed coin envelope. Unlike other known dental floss packages, the dental floss package 10 of the present invention is primarily two-dimensional, and while it may have a variety of dimensions, it is preferred that it have the approximate length and width of a credit card (e.g. 2-1/16"×3-5/16" and a nominal thickness less than 1/16"), but it can be made of any desired size. In FIG. 5, the overall thickness of the dispensing envelope 16 is somewhat exaggerated for clarity of illustration, but it will be recognized that in the preferred embodiment of the present invention, the actual thickness of the inner dispensing envelope 16 is quite thin because it defined by the small diameter of the floss 12 and the very small thicknesses of the plastic pouch 14 and the envelope walls 18 and 18'. The flat shape, the light weight and paper-like flexibility of the package 10 allows the consumer to store and transport it in a small, flat space such as a pocket, purse, or wallet for which a virtually two-dimensional container is advantageous.

In use, the dispensing envelope 16 is removed from the outer sleeve 32 and held in one hand, with the other hand being used to withdraw the desired amount of floss 12 from the inside of envelope 16 through the exit opening 38 from inside the envelope to the outside of the envelope 16. Once the desired amount of floss 12 is withdrawn, the floss 12 is cut by passing it beneath the exposed cutter blade 22 that is secured to the side wall 18' of the dispensing envelope 16. In the embodiment illustrated in FIG. 6, the die cut opening 28 in the flap 20 exposes an adhesive surface 30 that may be used to capture and hold the external loose end of the floss after cutting to secure the exposed floss end and prevent inadvertent floss withdrawal during storage and transport.

Some of the unique features of the present invention include the following. Even though the dispensing package 10 is small and flat, it can nevertheless contain a relatively large supply of dental floss 12 so that it can used over a long period of time, and during that time it can be readily and easily carried in the users wallet or the like as described above. While it is know to provide single strands of dental floss from a paper envelope as described above, these single strands are good for one use only, after which the dispenser is discarded, whereas with the present invention it is possible to cut to length a large number of floss pieces as needed, allowing for longer consumable life and greater advertising value. The plastic pouch 14 within the dispensing envelope 16 serves the purpose of retaining and composing a loose coil of floss 12 within the dispensing envelope. Moreover, as described above, the line of glue or other adhesive 24 is integrated into the assembly of the dispensing package and serves the dual purpose of securing the cutter blade 22 to the side wall 18' and also secures the flap 20 at its closed position. The small opening 28 in the flap 20 exposes an adhesive 30 that may be used to capture and hold the external loose end of the floss 12 after cutting to secure the exposed floss end and prevent inadvertent floss withdrawal during storage and transport (see FIG. 6). The dispensing envelope of the present invention has a generally flat shape, and it is thin and flexible so as to improve the comfort and practicality of storing it in a pocket, or wallet, or the like.

In view of the aforesaid written description of the present invention, it will be readily understood by those persons skilled in the art that the present invention is susceptible of broad utility and application. Many embodiments and adaptations of the present invention other than those herein described, as well as many variations, modifications, and equivalent arrangements, will be apparent from or reasonably suggested by the present invention and the foregoing description thereof, without departing from the substance or scope of the present invention. Accordingly, while the present invention has been described herein in detail in relation to preferred embodiments, it is to be understood that this disclosure is only illustrative and exemplary of the present invention and is made merely for purposes of providing a full and enabling disclosure of the invention. The foregoing disclosure is not intended nor is to be construed to limit the present invention or otherwise to exclude any such other embodiments, adaptations, variations, modifications and equivalent arrangements, the present invention being limited only by the claims appended hereto and the equivalents thereof.

What is claimed is:

1. A dental floss package for containing and dispensing a length of floss therefrom, the package including:
   (a) a dispensing envelope formed of thin material that includes two flat side walls having side edges and being folded over one another in overlapping relation to lie closely adjacent one another, the two overlapping side walls being joined directly to one another along side edges thereof, a flap portion joined to one of the side walls and folded over the other side wall to extend in parallel relation along the outer surface of the other side wall and secured to the outer surface, the flap portion having an opening therein, a cutter element mounted on the dispensing envelope and located so that it is at an exposed location extending through the opening in the flap portion, and an exit opening formed in the dispensing envelope through which dental floss can pass; and
   (b) a multi-use supply of dental floss contained within the dispensing envelope, and having one exposed end thereof passing out through the exit opening in the dispensing envelope and over an outer portion of the dispensing envelope to the cutter element, whereby a desired length of the dental floss may be withdrawn from the dispensing envelope by grasping the exposed end, pulling the desired length of dental floss from the package and cutting it using the cutter element.

2. A dental floss package as defined in claim 1, wherein the side walls are generally rectangular in shape with three side edges thereof glued together and with the other side edge being open, and wherein the flap portion is integrally formed with one of the side walls and is folded over the open side edges of the side walls.

3. A dental floss package as defined in claim 2, wherein the opening formed in the dispensing package is located at one side edge of the side walls of the dispensing envelope at the point where the flap portion is folded over the other side wall.

4. A dental floss package as defined in claim 3, wherein the flap portion is folded along a fold line located closely adjacent the open edge of the other wall to form the exit opening adjacent the open side edges of the side walls of the dispensing envelope.

5. A dental floss package as defined in claim 1, wherein the dental floss is formed in a flat spiral, and the dental floss is contained within a plastic pouch having an opening therein through which the dental floss can pass to the exit opening in the dispensing envelope.

6. A dental floss package as defined in claim 1, wherein the flap portion is formed with a second opening, and an adhesive is applied to the other side wall beneath the second opening so that the adhesive will be exposed through the second opening, whereby the end of the dental floss can be held in place by engagement with the adhesive.

7. A dental floss package as defined in claim 3, wherein an adhesive strip is located along the other side wall adjacent the open end of the dispensing envelope, wherein the cutter element is secured to a portion of the adhesive strip, and wherein the flap portion is secured to the other side wall by another portion of the adhesive strip.

8. A dental floss package as defined in claim 1, wherein the dispensing envelope is slideably contained in an outer sleeve whereby the dispensing envelope can maintained in the outer sleeve when not in use and easily removed from the outer sleeve when it is to be used.

9. A dental floss package as defined in claim 1, wherein a plastic pouch is located within the confines of the dispensing envelope, and the floss is arranged in a spiral configuration and contained within the plastic pouch except for an end of the floss that extends outwardly from the plastic pouch and out of the confines of the dispensing envelope.

10. A dental floss package for containing and dispensing a length of floss therefrom, the package including:
    (a) a dispensing envelope formed of thin material that includes two flat rectangular shaped side walls having four side edges and being folded over one another in overlapping relation to lie closely adjacent one another, the two overlapping side walls being joined directly to one another along three side edges thereof with the fourth side edge being open, a flap portion joined to one of the side walls and folded over the other side wall to extend in parallel relation to the other side wall along the outer surface of the other side wall and secured to the outer surface by an adhesive strip located therebetween, the flap portion having an opening formed therein, a cutter element mounted on the other side wall by the adhesive strip, the cutter element being located adjacent the opening in the flap portion and extending therethrough, and an exit opening formed in the dispensing envelope adjacent the open side edges of the two side walls and adjacent one side edge of the flap portion through which dental floss can pass;
    (b) a plastic pouch located within the confines of the dispensing envelope and having an opening therein; and
    (c) a multi-use supply of dental floss formed in a flat spiral configuration and contained within the plastic pouch, and having one exposed end thereof passing out through the opening in the plastic pouch and out through the exit opening in the dispensing envelope and over an outer surface of the flap portion of the dispensing envelope to the cutter element, whereby a desired length of the dental floss may be withdrawn from the dispensing envelope by grasping the exposed end, pulling the desired length of dental floss from the package and cutting it using the cutter element.

11. A dental floss package as defined in claim 10, wherein the flap portion is folded along a fold line located closely adjacent the open edge of the other wall to form the exit opening at the open side edges of the side walls of the dispensing envelope.

12. A dental floss package as defined in claim 10, wherein a small amount of adhesive is applied to the other side wall underneath the flap portion, and wherein the flap portion is formed with a second opening located to expose the small amount of adhesive whereby the end of the dental floss can be held in place by engagement with the adhesive.

13. A dental floss package as defined in claim 10, wherein the dispensing envelope is slideably contained in an outer sleeve whereby the dispensing envelope can maintained in the outer sleeve when not in use and easily removed from the outer sleeve when it is to be used.

* * * * *